(12) United States Patent
Rached et al.

(10) Patent No.: US 10,618,861 B2
(45) Date of Patent: *Apr. 14, 2020

(54) STABILIZATION OF 1-CHLORO-3,3,3-TRIFLUOROPROPENE

(71) Applicant: ARKEMA FRANCE, Colombes (FR)

(72) Inventors: Wissam Rached, Chaponost (FR); Sophie Guerin, Francheville (FR); Pascale Kindler, Fontaines sur Saone (FR)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,241

(22) Filed: Jul. 17, 2019

(65) Prior Publication Data

US 2019/0337874 A1 Nov. 7, 2019

Related U.S. Application Data

(63) Continuation of application No. 15/878,794, filed on Jan. 24, 2018, now Pat. No. 10,399,918, which is a continuation of application No. 15/073,108, filed on Mar. 17, 2016, now Pat. No. 9,908,828.

(30) Foreign Application Priority Data

Mar. 18, 2015 (FR) ..................... 15 52222

(51) Int. Cl.
C09K 5/04 (2006.01)
C07C 17/42 (2006.01)
F01K 25/10 (2006.01)

(52) U.S. Cl.
CPC .............. *C07C 17/42* (2013.01); *C09K 5/044* (2013.01); *F01K 25/10* (2013.01); *C09K 2205/12* (2013.01)

(58) Field of Classification Search
CPC .... C09K 5/044; C09K 5/045; C09K 2205/12; C09K 5/00; C09K 2205/126; C09K 2205/122; C09K 2205/22; C09K 15/20; C09K 2205/32; C09K 2205/40; C09K 2208/10; C09K 3/00; C09K 3/30; C09K 5/04; C09K 5/10; C09K 5/14; C09K 8/584; C09K 8/588
See application file for complete search history.

(56) References Cited

U.S. PATENT DOCUMENTS

| | | | |
|---|---|---|---|
| 5,065,990 A | 11/1991 | Durfee | |
| 5,363,674 A | 11/1994 | Powell | |
| 5,895,778 A | 4/1999 | McHenry et al. | |
| 6,814,884 B2 | 11/2004 | Jannick et al. | |
| 7,534,366 B2 | 5/2009 | Singh et al. | |
| 7,674,756 B2 | 3/2010 | Johnson | |
| 7,795,480 B2 | 9/2010 | Merkel et al. | |
| 8,058,486 B2 | 11/2011 | Merkel et al. | |
| 8,070,977 B2 | 12/2011 | Rached | |
| 8,075,798 B2 | 12/2011 | Rached | |
| 8,217,208 B2 | 7/2012 | Hulse et al. | |
| 8,246,850 B2 | 8/2012 | Rached | |
| 8,252,198 B2 | 8/2012 | Rached | |
| 8,323,524 B2 | 12/2012 | Flynn et al. | |
| 8,454,853 B2 | 6/2013 | Van Horn | |
| 8,557,135 B2 | 10/2013 | Rached | |
| 8,808,569 B2 | 8/2014 | Rached | |
| 8,858,824 B2 | 10/2014 | Boussand | |
| 8,858,825 B2 | 10/2014 | Guerin et al. | |
| 9,011,711 B2 | 4/2015 | Rached | |
| 9,028,706 B2 | 5/2015 | Rached et al. | |
| 9,039,922 B2 | 5/2015 | Rached | |
| 9,127,191 B2 | 9/2015 | Rached | |
| 9,133,379 B2 | 9/2015 | Rached | |
| 9,175,203 B2 | 11/2015 | Rached | |
| 9,267,064 B2 | 2/2016 | Rached | |
| 9,279,074 B2 | 3/2016 | Rached | |
| 9,315,708 B2 | 4/2016 | Guerin et al. | |
| 9,399,726 B2 | 7/2016 | Rached | |
| 9,505,968 B2 | 11/2016 | Rached | |
| 9,512,343 B2 | 12/2016 | Rached et al. | |
| 9,599,381 B2 | 3/2017 | Rached | |
| 9,650,551 B2 | 5/2017 | Collier et al. | |
| 9,650,553 B2 | 5/2017 | Deur-Bert et al. | |
| 9,663,697 B2 | 5/2017 | Rached | |
| 9,676,984 B2 | 6/2017 | Guerin et al. | |

(Continued)

FOREIGN PATENT DOCUMENTS

| | | |
|---|---|---|
| CN | 101155892 A | 4/2008 |
| EP | 2 119 759 A1 | 11/2009 |

(Continued)

OTHER PUBLICATIONS

U.S. Appl. No. 16/641,024, Rached, et al.
French Search Report dated Feb. 1, 2016, in the corresponding French Patent Application No. FR 1552222 (2 pages).
French Written Opinion (FR237) dated Feb. 1, 2016, in the corresponding French Patent Application No. FR 1552222 (3 pages).
Knunyants, I.L., et al., "Reactions of Fluoroolefins Communication. XIII. Catalytic hydrogenation of perfluoroolefins", Institute of Heteroorganic Compounds, Academy of Sciences of the USSR, No. 8, Aug. 1960 pp. 1312-1317 (English translation) (XP-002548816).
Copie Officielle (Certified Copy) of French Patent Application No. 0 955 139 filed 23 Jul. 2009, Certified copy dated 3 Jun. 2010, 28 pp., Inpi, Paris, Fr.

(Continued)

*Primary Examiner* — John R Hardee
(74) *Attorney, Agent, or Firm* — Buchanan Ingersoll & Rooney P.C.

(57) ABSTRACT

The use of a $C_3$ to $C_6$ alkene compound including a sole double bond, for limiting or preventing the isomerization of trans-1-chloro-3,3,3-trifluoropropene to cis-1-chloro-3,3,3-trifluoropropene. Also, a composition including 1-chloro-3,3,3-trifluoropropene and a $C_3$ to $C_6$ alkene compound including a sole double bond, and also to various uses of this composition, such as a process for heating or cooling a fluid.

26 Claims, No Drawings

(56) References Cited

U.S. PATENT DOCUMENTS

| | | |
|---|---|---|
| 9,683,155 B2 | 6/2017 | Deur-Bert et al. |
| 9,683,157 B2 | 6/2017 | Rached |
| 9,884,984 B2 | 2/2018 | Rached |
| 9,908,828 B2 * | 3/2018 | Rached .................. C07C 17/42 |
| 9,969,918 B2 | 5/2018 | Deur-Bert et al. |
| 10,023,780 B2 | 7/2018 | Guerin et al. |
| 10,035,938 B2 | 7/2018 | Rached |
| 10,036,285 B2 | 7/2018 | Rached |
| 10,119,055 B2 | 11/2018 | Boussand |
| 10,125,296 B2 | 11/2018 | Rached |
| 10,131,829 B2 | 11/2018 | Deur-Bert et al. |
| 10,252,913 B2 | 4/2019 | Bonnet et al. |
| 10,316,231 B2 | 6/2019 | Rached |
| 10,358,592 B2 | 7/2019 | Rached |
| 10,377,935 B2 | 8/2019 | Guerin et al. |
| 10,399,918 B2 * | 9/2019 | Rached .................. F01K 25/10 |
| 10,450,488 B2 | 10/2019 | Boussand |
| 2004/0256594 A1 | 12/2004 | Singh et al. |
| 2006/0243944 A1 | 11/2006 | Minor et al. |
| 2006/0243945 A1 | 11/2006 | Minor et al. |
| 2006/0266976 A1 | 11/2006 | Minor et al. |
| 2008/0098755 A1 | 5/2008 | Singh et al. |
| 2008/0111099 A1 | 5/2008 | Singh et al. |
| 2008/0135817 A1 | 6/2008 | Luly et al. |
| 2008/0230738 A1 | 9/2008 | Minor et al. |
| 2009/0030247 A1 | 1/2009 | Johnson et al. |
| 2009/0095014 A1 | 4/2009 | Sun et al. |
| 2009/0209791 A1 | 8/2009 | Van Der Puy |
| 2009/0305876 A1 | 12/2009 | Singh et al. |
| 2010/0012882 A1 | 1/2010 | Sherman et al. |
| 2010/0029997 A1 | 2/2010 | Wang et al. |
| 2010/0038582 A1 | 2/2010 | Shimomura et al. |
| 2010/0119460 A1 | 5/2010 | Pham et al. |
| 2010/0181524 A1 | 7/2010 | Elsheikh et al. |
| 2010/0205980 A1 | 8/2010 | Dixon et al. |
| 2010/0301259 A1 | 12/2010 | Leck et al. |
| 2011/0021849 A1 | 1/2011 | Avril et al. |
| 2011/0037016 A1 | 2/2011 | Singh et al. |
| 2011/0041530 A1 | 2/2011 | Mouli et al. |
| 2011/0084228 A1 | 4/2011 | Rached |
| 2011/0095224 A1 | 4/2011 | Rached |
| 2011/0186772 A1 | 8/2011 | Rached |
| 2011/0197602 A1 | 8/2011 | Abbas |
| 2011/0219791 A1 | 9/2011 | Rached |
| 2011/0219792 A1 | 9/2011 | Rached |
| 2011/0240254 A1 | 10/2011 | Rached |
| 2011/0284181 A1 | 11/2011 | Rached |
| 2012/0012591 A1 | 1/2012 | Bowman et al. |
| 2012/0049104 A1 | 3/2012 | Rached |
| 2012/0056123 A1 | 3/2012 | Rached |
| 2012/0065437 A1 | 3/2012 | Merkel |
| 2012/0068105 A1 | 3/2012 | Rached et al. |
| 2012/0117990 A1 | 5/2012 | Rached |
| 2012/0128964 A1 | 5/2012 | Hulse |
| 2012/0144857 A1 | 6/2012 | Rached |
| 2012/0151958 A1 | 6/2012 | Rached |
| 2012/0151959 A1 | 6/2012 | Rached |
| 2012/0153213 A1 | 6/2012 | Rached |
| 2012/0159982 A1 | 6/2012 | Rached |
| 2012/0161063 A1 | 6/2012 | Singh |
| 2012/0161064 A1 | 6/2012 | Rached |
| 2012/0167615 A1 | 7/2012 | Rached |
| 2012/0205574 A1 | 8/2012 | Rached et al. |
| 2012/0226081 A1 | 9/2012 | Elsheikh et al. |
| 2013/0004435 A1 | 1/2013 | Cook et al. |
| 2013/0092869 A1 | 4/2013 | Boussand |
| 2013/0105724 A1 | 5/2013 | Boussand |
| 2013/0186114 A1 | 7/2013 | Guerin et al. |
| 2014/0008565 A1 | 1/2014 | Rached et al. |
| 2014/0018582 A1 | 1/2014 | Sun et al. |
| 2014/0070129 A1 | 3/2014 | Kennoy et al. |
| 2014/0075969 A1 | 3/2014 | Guerin et al. |
| 2014/0318160 A1 | 10/2014 | Rached |
| 2014/0326017 A1 | 11/2014 | Rached |
| 2015/0027146 A1 | 1/2015 | Boussand |
| 2015/0034523 A1 | 2/2015 | Kopkalli et al. |
| 2015/0152306 A1 | 6/2015 | Rached |
| 2015/0152307 A1 | 6/2015 | Rached |
| 2015/0231527 A1 | 8/2015 | Singh |
| 2015/0322317 A1 | 11/2015 | Collier et al. |
| 2015/0322321 A1 | 11/2015 | Deur-Bert et al. |
| 2015/0344761 A1 | 12/2015 | Rached |
| 2015/0353799 A1 | 12/2015 | Deur-Bert et al. |
| 2015/0353802 A1 | 12/2015 | Rached |
| 2016/0009555 A1 | 1/2016 | Bonnet et al. |
| 2016/0023034 A1 | 1/2016 | Elsheikh et al. |
| 2016/0024363 A1 | 1/2016 | Rached |
| 2016/0025394 A1 | 1/2016 | Rached |
| 2016/0115361 A1 | 4/2016 | Boussand |
| 2016/0122609 A1 | 5/2016 | Rached |
| 2016/0194541 A1 | 7/2016 | Guerin et al. |
| 2016/0244652 A1 | 8/2016 | Rached |
| 2016/0272561 A1 | 9/2016 | Rached et al. |
| 2016/0298014 A1 | 10/2016 | Rached |
| 2016/0355718 A1 | 12/2016 | Rached |
| 2016/0376484 A1 | 12/2016 | Guerin et al. |
| 2017/0037291 A1 | 2/2017 | Rached et al. |
| 2017/0080773 A1 | 3/2017 | Rached |
| 2017/0145276 A1 | 5/2017 | Rached |
| 2017/0210960 A1 | 7/2017 | Deur-Bert et al. |
| 2017/0210962 A1 | 7/2017 | Collier et al. |
| 2017/0218241 A1 | 8/2017 | Deur-Bert et al. |
| 2017/0218242 A1 | 8/2017 | Rached |
| 2018/0086173 A1 | 3/2018 | Rached |
| 2018/0134936 A1 | 5/2018 | Rached |
| 2018/0148395 A1 | 5/2018 | Rached et al. |
| 2018/0244970 A1 | 8/2018 | Rached |
| 2018/0282603 A1 | 10/2018 | Guerin et al. |
| 2018/0320560 A1 | 11/2018 | Rached |
| 2018/0327645 A1 | 11/2018 | Boussand |
| 2019/0023957 A1 | 1/2019 | Rached |
| 2019/0040292 A1 | 2/2019 | Rached |
| 2019/0048241 A1 | 2/2019 | Abbas et al. |
| 2019/0048518 A1 | 2/2019 | Wong et al. |
| 2019/0203094 A1 | 7/2019 | Rached |
| 2019/0249057 A1 | 8/2019 | Rached |
| 2019/0276721 A1 | 9/2019 | Rached |
| 2019/0284500 A1 | 9/2019 | Rached |
| 2019/0359870 A1 | 11/2019 | Rached |
| 2019/0367789 A1 | 12/2019 | Rached |

FOREIGN PATENT DOCUMENTS

| | | |
|---|---|---|
| EP | 2 149 543 A1 | 2/2010 |
| EP | 2 281 792 A1 | 2/2011 |
| JP | S62-225860 A | 10/1987 |
| JP | H03-168566 A | 7/1991 |
| JP | H04-110388 A | 4/1992 |
| JP | H06-272978 A | 9/1994 |
| JP | 2002-501035 A | 1/2002 |
| JP | 2008-524433 A | 7/2008 |
| JP | 2008-531836 A | 8/2008 |
| JP | 2010-037343 A1 | 2/2010 |
| JP | 2010-133401 | 6/2010 |
| JP | 2011-510119 A | 3/2011 |
| WO | WO 99/37598 A1 | 7/1999 |
| WO | WO 02/40613 A1 | 5/2002 |
| WO | WO 2004/037913 A2 | 5/2004 |
| WO | WO 2004/037913 A3 | 5/2004 |
| WO | WO 2006/069362 A2 | 6/2006 |
| WO | WO 2006/069362 A3 | 6/2006 |
| WO | WO 2006/094303 A2 | 9/2006 |
| WO | WO 2006/094303 A3 | 9/2006 |
| WO | WO 2007/002625 A2 | 1/2007 |
| WO | WO 2007/002625 A3 | 1/2007 |
| WO | WO 2007/126414 A2 | 11/2007 |
| WO | WO 2007/126414 A3 | 11/2007 |
| WO | WO 2008/027515 A2 | 3/2008 |
| WO | WO 2008/027515 A3 | 3/2008 |
| WO | WO 2008/027516 A1 | 3/2008 |
| WO | WO 2008/027596 A2 | 3/2008 |
| WO | WO 2008/027596 A3 | 3/2008 |

(56) References Cited

FOREIGN PATENT DOCUMENTS

| WO | WO 2008/030439 A2 | 3/2008 |
|---|---|---|
| WO | WO 2008/030440 A2 | 3/2008 |
| WO | WO 2008/042066 A1 | 4/2008 |
| WO | WO 2009/003165 A1 | 12/2008 |
| WO | WO 2009/137656 A1 | 11/2009 |
| WO | WO 2009/140231 A2 | 11/2009 |
| WO | WO 2010/008640 A1 | 1/2010 |
| WO | WO 2010/029704 A1 | 3/2010 |
| WO | WO 2010/043807 A1 | 4/2010 |
| WO | WO 2010/056695 A2 | 5/2010 |
| WO | WO 2010/059677 A2 | 5/2010 |
| WO | WO 2010/059677 A3 | 5/2010 |
| WO | WO 2010/064011 A1 | 6/2010 |
| WO | WO 2010/075046 A2 | 7/2010 |
| WO | WO 2012/004487 A2 | 1/2012 |
| WO | WO 2012/004487 A3 | 1/2012 |
| WO | WO 2014/158663 A1 | 10/2014 |

OTHER PUBLICATIONS

International Search Report and Written Opinion dated Feb. 2, 2016 in PCT/FR2016/050577, European Patent Office, Rijswijk, NL, French and English-language translation, 15 pages.

Yamamoto, Hiroyasu, et al., "Compression Type Heat Pump", Application and Economy of Heat Pump, Technical Report, No. 52, Chapter 4, Feb. 27, 1984, pp. 117-134 (22 pages including Partial English-language translation).

Zheng, Zuyi, *Application of Heat Pump Technology in Air Conditioning*, China Mechanical Press, 1st edition, Jul. 1998, five pages including p. 9, title page, publisher information, and English-language translation of p. 9.

Xiuling, Yuan, Editor, *Refrigeration and Air-Conditioning Apparatus*, Xi'an Jiaotong University Press, 1 $^{st}$ edition, Mar. 2001, four pages including p. 37, title page, publisher information, and English-language translation of p. 37.

**Rached, Wissam, et al., U.S. Appl. No. 16/641,024, entitled "Composition on the Basis of Hydrochlorofluoroolefin and Mineral Oil," filed Feb. 21, 2020.

* cited by examiner

STABILIZATION OF 1-CHLORO-3,3,3-TRIFLUOROPROPENE

CROSS REFERENCE TO RELATED APPLICATIONS

The present application is a continuation of U.S. application Ser. No. 15/878,794, now U.S. Pat. No. 10,399,918, filed on Jan. 24, 2018, which is a continuation of U.S. application Ser. No. 15/073,108, filed on Mar. 17, 2016, now U.S. Pat. No. 9,908,828, which claims the benefit of French Application No. 1552222, filed on Mar. 18, 2015. The entire contents of each of U.S. application Ser. No. 15/878,794, U.S. application Ser. No. 15/073,108 and French Application No. 1552222 are hereby incorporated herein by reference in their entirety.

FIELD OF THE INVENTION

The present invention relates to compounds which make it possible to stabilize 1-chloro-3,3,3-trifluoroproprene and more specifically to limit or prevent isomerization of the trans form to the cis form. The invention also relates to the use of such stabilizers in heat-transfer applications.

TECHNICAL BACKGROUND

Trans-1-chloro-3,3,3-trifluoroproprene (HCFO-1233zdE) is a product with a low global warming potential (GWP). It has thermodynamic and thermophysical properties that are very favorable for use as a heat-transfer fluid in cooling, air-conditioning, electricity production (in particular by means of organic Rankine cycles) and high-temperature heat pump applications.

HCFO-1233zdE has an instability which manifests itself especially at relatively high temperature. This instability consists of an isomerization of a fraction of the initial feedstock resulting in the formation of cis-1-chloro-3,3,3-trifluoroproprene (HCFO-1233zdZ).

As it happens, HCFO-1233zdZ is a less volatile product than HCFO-1233zdE. The boiling point is about 40° C. for the Z isomer, and about 18.3° C. for the E isomer. This difference implies a change in the thermodynamic and thermophysical properties of the product in facilities, and a loss of performance level, when the isomerization occurs.

Document WO 2009/003165 describes the risks of degradation of hydrofluoroolefins and hydrochlorofluoroolefins, and also stabilizers for combating this degradation. These stabilizers comprise free radical scavenger compounds, acid scavenger compounds, oxygen scavenger compounds and polymerization inhibitors. Mention is in particular made of: 1,2-epoxybutane, glycidyl methyl ether, d-1-limonene oxide, 1,2-epoxymethylpropane, nitromethane, alpha-methylstyrene, isoprene, phenol, hydroquinones and hydrazine.

Document U.S. Pat. No. 7,795,480 describes a process for producing 2-chloro-3,3,3-trifluoropropene (HCFO-1233xf). A phenomenon of polymerization of the compound is mentioned (but not an isomerization phenomenon). Proposed stabilizers are p-tap(4-tert-amylphenol), methoxyhydroquinone, 4-methoxyphenol, triethylamine, diisopropylamine, butylated hydroxyanisole and thymol.

Document U.S. Pat. No. 8,217,208 describes the phenomenon of isomerization of HFO-1233zdE under the effect of temperature, but it does not teach stabilizers which make it possible to limit this isomerization.

Document US 2012/0226081 describes the risks of degradation of hydrochloroolefins and of hydrochloroalkanes, and proposes a set of possible stabilizers: alpha-methylstyrene, alpha-pineneoxide, beta-pineneoxide, 1,2-epoxybutane, 1,2-hexadecene oxide and oxygen scavenger compounds such as diethylhydroxylamine, hydroquinone, methylethylketooxime and p-methoxyphenol.

Document US 2015/0034523 describes the risks of degradation of hydrochloroolefins and proposes two families of stabilizers, namely morpholines or trialkyl phosphates.

Virtually all of the stabilizers proposed in the prior art are solid products, or liquid products with a high boiling point. For example, the boiling point of alpha-methylstyrene is 165° C., the boiling point of limonene oxide is greater than 200° C., etc.

Isoprene, mentioned in document WO 2009/003165, is for its part a product that is unstable in itself, and that must generally be combined with a compound such as 4-tert-butylpyrocatechol in order to prevent it from being polymerized.

The characteristics described above make the stabilizers unsuitable for certain applications in which HCFO-1233zdE is liable to be used. This is in particular the case with applications using flooded evaporators (in particular with compressors without lubricating oil). In such applications, the prior art stabilizers, with a high boiling point, are ineffective since they concentrate in the evaporator and do not migrate with the heat-transfer fluid to the condenser.

There is therefore a need to provide stabilizers which make it possible to limit or prevent the isomerization of HCFO-1233zdE to HCFO-1233zdZ, in particular in vapor compression systems such as air-conditioning, refrigeration, heat-pump and organic Rankine cycle systems, and quite particularly systems comprising a flooded evaporator.

SUMMARY OF THE INVENTION

The invention relates firstly to the use of a $C_3$ to $C_6$ alkene compound comprising a sole double bond, for limiting or preventing the isomerization of trans-1-chloro-3,3,3-trifluoropropene to cis-1-chloro-3,3,3-trifluoropropene.

According to one embodiment, the alkene compound is a butene or a pentene.

According to one embodiment, the alkene compound has:
a boiling point less than or equal to 100° C., preferably less than or equal to 75° C., and more particularly preferably less than or equal to 50° C.; and/or
a solidification temperature less than or equal to 0° C., preferably less than or equal to −25° C., and more particularly preferably less than or equal to −50° C.

According to one embodiment, the alkene compound is 2-methylbut-2-ene.

According to one embodiment, the alkene compound is 3-methylbut-1-ene.

A subject of the invention is also a composition comprising 1-chloro-3,3,3-trifluoropropene and a $C_3$ to $C_6$ alkene compound comprising a sole double bond.

According to one embodiment, the alkene compound is a butene or a pentene.

According to one embodiment, the alkene compound has:
a boiling point less than or equal to 100° C., preferably less than or equal to 75° C., and more particularly preferably less than or equal to 50° C.; and/or
a solidification temperature less than or equal to 0° C., preferably less than or equal to −25° C., and more particularly preferably less than or equal to −50° C.

According to one embodiment, the alkene compound is 2-methylbut-2-ene.

According to one embodiment, the alkene compound is 3-methylbut-1-ene.

According to one embodiment, the compound comprises from 0.01% to 5%, preferably from 0.1% to 2% and more particularly from 0.2% to 1%, by weight, of alkene compound.

According to one embodiment, the 1-chloro-3,3,3-trifluoropropene is in trans form in a weight proportion greater than or equal to 90%, preferably greater than or equal to 95%, more particularly preferably greater than or equal to 98%, even more particularly preferably greater than or equal to 99%, and ideally greater than or equal to 99.5%, or even greater than 99.9%.

According to one embodiment, the composition also comprises one or more heat-transfer compounds other than 1-chloro-3,3,3-trifluoropropene and/or one or more additives chosen from stabilizers other than the alkene compound, lubricants, surfactants, tracers, fluorescent agents, odorous agents, solubilizing agents, and mixtures thereof.

A subject of the invention is also the use of the above composition as a heat-transfer fluid in a vapor compression system.

According to one embodiment, the vapor compression system is:
an air-conditioning system; or
a refrigeration system; or
a freezing system; or
a heat pump system.

According to one embodiment, the above use is a use as a heat-transfer fluid in a thermal engine.

According to one embodiment, the heat-transfer fluid is at a temperature greater than or equal to 100° C., preferably greater than or equal to 140° C., more particularly preferably greater than or equal to 180° C., for at least one fraction of the duration of its use.

According to one embodiment, the heat-transfer fluid is evaporated in a flooded evaporator.

A subject of the invention is also a heat-transfer facility comprising a circuit containing the above composition as a heat-transfer fluid.

According to one embodiment, the facility is chosen from mobile or stationary facilities for heating via a heat pump, for air-conditioning, for refrigeration, or for freezing and thermal engines.

According to one embodiment, the facility comprises a flooded evaporator.

A subject of the invention is also a process for heating or cooling a fluid or a body by means of a vapor compression system containing a heat-transfer fluid, said process comprising successively the evaporation of the heat-transfer fluid, the compression of the heat-transfer fluid, the condensation of the heat-transfer fluid and the expansion of the heat-transfer fluid, in which the heat-transfer fluid is the composition described above.

A subject of the invention is also a process for producing electricity by means of a thermal engine, said process comprising successively the evaporation of the heat-transfer fluid, the expansion of the heat-transfer fluid in a turbine which makes it possible to generate electricity, the condensation of the heat-transfer fluid and the compression of the heat-transfer fluid, in which the heat-transfer fluid is the composition described above.

The present invention makes it possible to overcome the drawbacks of the prior art. It provides more particularly stabilizers which make it possible to limit or prevent the isomerization of HCFO-1233zdE to HCFO-1233zdZ, in particular in vapor compression systems such as air-conditioning, refrigeration, heat pump and thermal engine systems, and quite particularly the systems comprising a flooded evaporator.

DESCRIPTION OF EMBODIMENTS OF THE INVENTION

The invention is now described in greater detail and in a nonlimiting manner in the description which follows.

Unless otherwise mentioned, throughout the application, the proportions of compounds indicated are given as weight percentages.

The invention is based on the discovery that $C_3$ to $C_6$ alkene compounds comprising a sole double bond make it possible to stabilize HCFO-1233zdE, i.e. to limit or prevent the isomerization thereof to HCFO-1233zdZ, in particular at high temperatures.

The stabilizing compounds of the invention are therefore propene, butenes, pentenes and hexenes. Butenes and pentenes are preferred. Pentenes are even more particularly preferred.

The stabilizing compounds of the invention may comprise a linear or branched chain and preferably a branched chain.

Preferably, they have a boiling point less than or equal to 100° C., more preferably less than or equal to 75° C., and more particularly preferably less than or equal to 50° C.

The term "boiling point" is intended to mean the boiling point at a pressure of 101.325 kPa, as determined according to standard NF EN 378-1 from April 2008.

Likewise preferably, they have a solidification temperature less than or equal to 0° C., preferably less than or equal to −25° C., and more particularly preferably less than or equal to −50° C.

The solidification temperature is determined according to Test No. 102: Melting point/Melting range (OECD guidelines for the testing of chemicals, Section 1, OECD publications, Paris, 1995, available at the web address httplidx.doi.org/10.1787/9789264069534-fr).

Stabilizing compounds of the invention are in particular:
but-1-ene;
cis-but-2-ene;
trans-but-2-ene;
2-methylprop-1-ene;
pent-1-ene;
cis-pent-2-ene;
trans-pent-2-ene;
2-methylbut-1-ene;
2-methylbut-2-ene; and
3-methylbut-1-ene.

Among the preferred compounds are in particular 2-methylbut-2-ene, of formula $(CH_3)_2C=CH-CH_3$ (boiling point of approximately 39° C.), and 3-methylbut-1-ene, of formula $CH_3-CH(CH_3)-CH=CH_2$ (boiling point of approximately 25° C.).

Two or more than two of the above compounds may also be used in combination. The stabilizing compounds according to the invention are thus advantageously used in combination with HCFO-1233zd, and more particularly with HCFO-1233zdE, in heat-transfer applications.

Thus, the invention provides a composition, in particular of use for heat-transfer applications, comprising at least HCFO-1233zd and a stabilizing compound described above.

The weight proportion of the stabilizing compounds above in the composition may in particular be: from 0.01% to 0.05%; or from 0.05% to 0.1%; or from 0.1% to 0.2%; or from 0.2% to 0.3%; or from 0.3% to 0.4%; or from 0.4% to 0.5%; or from 0.5% to 0.6%; or from 0.6% to 0.7%; or from 0.7% to 0.8%; or from 0.8% to 0.9%; or from 0.9% to 1%; or from 1% to 1.2%; or from 1.2% to 1.5%; or from 1.5% to 2%; or from 2% to 3%; or from 3% to 4%; or from 4% to 5%.

The composition may comprise HCFO-1233zdE and optionally HCFO-1233zdZ. Advantageously, the proportion of HCFO-1233zdE, relative to the total HCFO-1233zd, is greater than or equal to 90%, or greater than or equal to 91%, or greater than or equal to 92%, or greater than or equal to 93%, or greater than or equal to 94%, or greater than or equal to 95%, or greater than or equal to 96%, or greater than or equal to 97%, or greater than or equal to 98%, or greater than or equal to 99%, or greater than or equal to 99.1%, or greater than or equal to 99.2%, or greater than or equal to 99.3%, or greater than or equal to 99.4%, or greater than or equal to 99.5%, or greater than or equal to 99.6%, or greater than or equal to 99.7%, or greater than or equal to 99.8%, or greater than or equal to 99.9%, or greater than or equal to 99.91%, or greater than or equal to 99.92%, or greater than or equal to 99.93%, or greater than or equal to 99.94%, or greater than or equal to 99.95%, or greater than or equal to 99.96%, or greater than or equal to 99.97%, or greater than or equal to 99.98%, or greater than or equal to 99.99%.

The presence of the stabilizing compound makes it possible to limit or prevent an increase in the proportion of HCFO-1233zdZ in the composition over time and/or in the event of the application of relatively high temperatures.

The composition of the invention may also comprise various additives. When it is a heat-transfer composition, the additives may in particular be chosen from lubricants, nanoparticles, stabilizers (other than the stabilizing compounds of the invention), surfactants, tracers, fluorescent agents, odorous agents and solubilizing agents.

The stabilizer(s), when it (they) is (are) present, preferably represent(s) at most 5% by weight in the heat-transfer composition. Among the stabilizers, mention may in particular be made of nitromethane, ascorbic acid, terephthalic acid, azoles such as tolutriazole or benzotriazole, phenolic compounds such as tocopherol, hydroquinone, t-butylhydroquinone, 2,6-di-tert-butyl-4-methylphenol, epoxides (alkyl optionally fluorinated or perfluorinated or alkenyl or aromatic) such as n-butyl glycidyl ether, hexanediol diglycidyl ether, allyl glycidyl ether, or butyl phenyl glycidyl ether, phosphites, phosphonates, thiols and lactones.

By way of lubricants, use may in particular be made of oils of mineral origin, silicone oils, paraffins of natural origin, naphthenes, synthetic paraffins, alkylbenzenes, poly-alpha-olefins, polyalkene glycols, polyol esters and/or polyvinyl ethers.

According to one advantageous embodiment of the invention, the composition of the invention is, however, free of lubricant.

By way of nanoparticles, use may in particular be made of carbon nanoparticles, metal (copper, aluminum) oxides, $TiO_2$, $Al_2O_3$, $MoS_2$, etc.

By way of tracers (capable of being detected), mention may be made of deuterated or non-deuterated hydrofluorocarbons, deuterated hydrocarbons, perfluorocarbons, fluoroethers, brominated compounds, iodinated compounds, alcohols, aldehydes, ketones, nitrous oxide and combinations thereof. The tracer is other than the heat-transfer compound(s) making up the heat-transfer fluid.

By way of solubilizing agents, mention may be made of hydrocarbons, dimethyl ether, polyoxyalkylene ethers, amides, ketones, nitriles, chlorocarbons, esters, lactones, aryl ethers, fluoroethers and 1,1,1-trifluoroalkanes. The solubilizing agent is other than the heat-transfer compound(s) making up the heat-transfer fluid.

By way of fluorescent agents, mention may be made of naphthalimides, perylenes, coumarins, anthracenes, phenanthracenes, xanthenes, thioxanthenes, naphthoxanthenes, fluoresceins and derivatives and combinations thereof.

By way of odorous agents, mention may be made of alkyl acrylates, allyl acrylates, acrylic acids, acrylesters, alkyl ethers, alkyl esters, alkynes, aldehydes, thiols, thioethers, disulfides, allylisothiocyanates, alkanoic acids, amines, norbornenes, norbornene derivatives, cyclohexene, heterocyclic aromatic compounds, ascaridol, o-methoxy(methyl)phenol and combinations thereof.

The composition according to the invention may also comprise at least one other heat-transfer compound, in addition to the HCFO-1233zd. Such other optional heat-transfer compound may in particular be a hydrocarbon, ether, hydrofluoroether, hydrofluorocarbon, hydrochlorofluorocarbon, hydrofluoroolefin, hydrochloroolefin or hydrochlorofluoroolefin compound.

By way of example, said other heat-transfer compound may be chosen from 1,1,1,4,4,4-hexafluorobut-2-ene (HFO-1336mmz, E or Z isomer), 3,3,4,4,4-pentafluorobut-1-ene (HFO-1345fz), 2,4,4,4-tetrafluorobut-1-ene (HFO-1354mfy), 1,1,1,3,3-pentafluoropropane (HFC-245fa), 2,3,3,3-tetrafluoropropene (HFO-1234yf), 1,3,3,3-tetrafluoropropene (HFC-1234ze), difluoromethane (HFC-32), 1,1,1,2-tetrafluoroethane (HFC-134a), 1,1,2,2-tetrafluoroethane (HFC-134), 1,1-difluoroethane (HFC-152a), pentafluoroethane (HFC-125), 1,1,1,3,3-pentafluorobutane (HFC-365mfc), methoxynonafluorobutane (HFE7100), butane (HC-600), 2-methylbutane (HC-601a), pentane (HC-601), ethyl ether, methyl acetate and combinations thereof.

In the composition of the invention, the HCFO-1233zd may represent in particular from 1% to 5% of the composition; or from 5% to 10% of the composition; or from 10% to 15% of the composition; or from 15% to 20% of the composition; or from 20% to 25% of the composition; or from 25% to 30% of the composition; or from 30% to 35% of the composition; or from 35% to 40% of the composition; or from 40% to 45% of the composition; or from 45% to 50% of the composition; or from 50% to 55% of the composition; or from 55% to 60% of the composition; or from 60% to 65% of the composition; or from 65% to 70% of the composition; or from 70% to 75% of the composition; or from 75% to 80% of the composition; or from 80% to 85% of the composition; or from 85% to 90% of the composition; or from 90% to 95% of the composition; or from 95% to 99% of the composition; or from 99% to 99.5% of the composition; or from 99.5% to 99.9% of the composition; or more than 99.9% of the composition. The HCFO-1233zd content may also vary within several of the above ranges: for example, from 50% to 55% and from 55% to 60%, i.e. from 50% to 60%, etc.

The composition of the invention can be used in a heat transfer process.

The heat transfer process according to the invention is based on the use of a facility comprising a vapor compression system which contains the composition of the invention as heat-transfer fluid. The heat transfer process may be a process for heating or cooling a fluid or a body.

The composition of the invention may also be used in a process for producing mechanical working or electricity, in particular in accordance with a Rankine cycle.

For the heating and cooling applications, the vapor compression system comprises at least one evaporator, one compressor, one condenser and one expansion valve, and also lines for transporting heat-transfer fluid between these components. The evaporator and the condenser comprise a heat exchanger making it possible to exchange heat between the heat-transfer fluid and another fluid or body.

By way of compressor, use may in particular be made of a centrifugal compressor having one or more stages or of a centrifugal mini-compressor. Rotary compressors, spiral compressors, reciprocating compressors or screw compressors may also be used. The compressor may be driven by an electric motor or by a gas turbine (for example fed by the exhaust gases of a vehicle, for mobile applications) or by gearing.

The vapor compression system then operates according to a conventional vapor compression cycle. The cycle comprises the change of state of the heat-transfer fluid from a liquid phase (or liquid/vapor phase state) to a vapor phase at a relatively low pressure, then the compression of the fluid in the vapor phase up to a relatively high pressure, the change of state (condensation) of the heat-transfer fluid from the vapor phase to the liquid phase at a relatively high pressure, and the reduction of the pressure so as to recommence the cycle.

The facility may also optionally comprise at least one circuit of heat-transfer fluid used to transmit the heat (with or without change of state) between the heat-transfer fluid circuit and the fluid or body to be heated or cooled.

The facility may also optionally comprise two (or more) vapor compression systems, containing identical or distinct heat-transfer fluids. For example, the vapor compression systems may be coupled to one another.

The cooling processes and facilities according to the invention comprise processes and facilities for air-conditioning (with mobile facilities, for example in vehicles, or stationary facilities), for refrigeration (with mobile facilities for example in containers, or stationary facilities) and for freezing or for cryogenics.

The heating facilities according to the invention comprise heat pumps.

For the applications for producing mechanical working or electricity, the facility is a thermal engine, which comprises at least one evaporator, one turbine, one condenser and one pump, and also lines for transporting heat-transfer fluid between these components. The facility can then operate according to a Rankine cycle.

It is possible to use any type of heat exchanger for the implementation of the heat-transfer fluids according to the invention, and in particular concurrent heat exchangers, or, preferably, countercurrent heat exchangers.

In particular, the evaporator used in the context of the invention may be a superheating evaporator or a flooded evaporator. In a superheating evaporator, all of the heat-transfer fluid is evaporated at the evaporator outlet, and the vapor phase is superheated.

In a flooded evaporator, the heat-transfer fluid in liquid form does not completely evaporate. A flooded evaporator comprises a liquid phase/vapor phase separator.

The invention is particularly of use when such an evaporator is used. This is because the prior art stabilizers with a high boiling point are ineffective when such an evaporator is used, since they concentrate in the evaporator and do not migrate with the heat-transfer fluid to the condenser.

The invention is also particularly of use when a high temperature exists at at least one point of the fluid circuit, and more particularly a temperature greater than or equal to 100° C., or greater than or equal to 110° C., or greater than or equal to 120° C., or greater than or equal to 130° C., or greater than or equal to 140° C., or greater than or equal to 150° C., or greater than or equal to 160° C., or greater than or equal to 170° C., or greater than or equal to 180° C., or greater than or equal to 190° C., or greater than or equal to 200° C. This is because it is under these conditions that HCFO-1233zdE is most likely to be converted into HCFO-1233zdZ.

In particular, in air-conditioning equipment, the general operating temperature is less than 100° C.; however, hot points at the compressor outlet may reach temperatures greater than 100° C., affecting the heat-transfer fluid over the course of a small proportion of its complete circulation time (for example less than 1%).

In heat pumps, the condensation temperature may reach approximately 140° C. In this case, the heat-transfer fluid may be at a temperature of approximately 140° C. over the course of a large proportion of its complete circulation time (for example approximately 50%). Furthermore, hot points between 150 and 200° C. may also be noted at the compressor outlet. The impact of a long residence time at temperatures greater than 100° C. and the existence of points at temperatures which may be in the region of 200° C. therefore require a stabilizer.

Likewise preferably, in the facility according to the invention, the temperature of the composition used as heat-transfer fluid remains greater than the solidification temperature of the stabilizing compound, in order to prevent any deposit of solid material in the circuit.

The composition according to the invention may also be of use as a blowing agent, a propellant (for example for an aerosol), a cleaning agent or solvent, or a dielectric gas, in addition to its use as a heat-transfer fluid.

As a propellant, the composition according to the invention may be used alone or in combination with known propellants. The propellant comprises, preferably consists of, a composition according to the invention. The active substance that must be propelled can be mixed with the propellant and inert compounds, solvents or other additives, so as to form a composition to be propelled. Preferably, the composition to be propelled is an aerosol.

As a blowing agent, the composition according to the invention may be included in a blowing composition, which preferably comprises one or more other compounds capable of reacting and of forming a foam or cellular structure under appropriate conditions, as is known to those skilled in the art.

In particular, the invention provides a process for preparing an expanded thermoplastic product comprising, first, the preparation of a polymeric blowing composition. Typically, the polymeric blowing composition is prepared by plasticizing a polymer resin and by mixing in the compounds of a blowing agent composition at an initial pressure. The plasticizing of the polymer resin can be carried out under the effect of heat, by heating the polymer resin in order to soften it sufficiently to mix in a blowing agent composition. Generally, the plasticizing temperature is close to the glass transition temperature or to the melting point for the crystalline polymers.

Other uses of the composition according to the invention comprise uses as a solvent, cleaning agent or the like. Mention may, for example, be made of vapor degreasing, precision cleaning, the cleaning of electronic circuits, dry cleaning, abrasive cleaning, solvents for the deposition of lubricants and release agents, and other solvent or surface treatments.

EXAMPLES

The following examples illustrate the invention without limiting it.

Example 1 (Comparative)-Instability of HCFO-1233zdE in the Absence of Stabilizer The tests for thermal stability of HCFO-1233zdE are carried out according to the standard ASHRAE 97-2007 entitled "Sealed glass tube method to test the chemical stability of materials for use within refrigerant systems".

The compositions are determined by gas chromatography on a CP-sil8-CB column.

A first series of tests is carried out at 150° C. for times of between 10 minutes and 14 days. The results show a slight formation of the HFO-1233zdZ isomer, up to a content of 0.14% being reached at 14 days.

A second series of tests is carried out at 200° C. for a time of 24 hours. The results show a slight formation of the HCFO-1233zdZ isomer up to a content of approximately 1% being reached.

Finally, a third series of tests is also carried out at 250° C. for a time of 24 hours. The results show a formation of the HCFO-1233zdZ isomer of between 6% and 9%.

Example 2 (invention)-Stabilization of HCFO-1233zdE

Thermal stability tests similar to those of example 1 are carried out, while adding 0.5% of stabilizer to the HCFO-1233zdE (weight content relative to the sum of the stabilizer and of the HCFO-1233zdE). The stabilizers tested are 2-methylbut-2-ene (2m2b) and 3-methylbut-1-ene (3m1b).

A first series of tests is carried out at 150° C. for a time of 14 days. The tests with 3m1b show a formation of the HCFO-1233zdZ isomer of about 0.08% at the end of the period. In the tests with 2m2b, no HFO-1233zd-Z formation is measured.

A second series of tests is carried out at 200° C. for a time of 24 hours. The tests with 3m1b show a slight formation of the HFO-1233zdZ isomer of about 0.3%, and those with 2m2b show an HCFO-1233zdZ formation of about 0.07% at the end of this period.

The following table summarizes the stabilization effect observed:

|  | HCFO-1233zdE alone | HCFO-1233zdE + 3m1b | HCFO-1233zdE + 2m2b |
| --- | --- | --- | --- |
| 14 days at 150° C. | 0.14% of HCFO-1233zdZ | 0.08% of HCFO-1233zdZ | HCFO-1233zdZ undetectable |
| 24 hours at 200° C. | 1% of HCFO-1233zdZ | 0.3% of HCFO-1233zdZ | 0.07% of HCFO-1233zdZ |

EMBODIMENTS

1. The use of a $C_3$ to $C_6$ alkene compound comprising a sole double bond, for limiting or preventing the isomerization of trans-1-chloro-3,3,3-trifluoropropene to cis-1-chloro-3,3,3-trifluoropropene.

2. The use as in embodiment 1, wherein the alkene compound is a butene or a pentene.

3. The use as in embodiment 1 or 2, wherein the alkene compound has:

a boiling point less than or equal to 100° C., preferably less than or equal to 75° C., and more particularly preferably less than or equal to 50° C.; and/or a solidification temperature less than or equal to 0° C., preferably less than or equal to −25° C., and more particularly preferably less than or equal to −50° C.

4. The use as in embodiment 1, wherein the alkene compound is 2-methylbut-2-ene.

5. The use as in embodiment 1, wherein the alkene compound is 3-methylbut-1-ene.

6. A composition comprising 1-chloro-3,3,3-trifluoropropene and a $C_3$ to $C_6$ alkene compound comprising a sole double bond.

7. The composition as in embodiment 6, wherein the alkene compound is a butene or a pentene.

8. The composition as in embodiment 6 or 7, wherein the alkene compound has:

a boiling point less than or equal to 100° C., preferably less than or equal to 75° C., and more particularly preferably less than or equal to 50° C.; and/or a solidification temperature less than or equal to 0° C., preferably less than or equal to −25° C., and more particularly preferably less than or equal to −50° C.

9. The composition as in embodiment 6, wherein the alkene compound is 2-methylbut-2-ene.

10. The composition as in embodiment 6, wherein the alkene compound is 3-methylbut-1-ene.

11. The composition as in one of embodiments 6 to 10, comprising from 0.01% to 5%, preferably from 0.1% to 2% and more particularly from 0.2% to 1%, by weight, of alkene compound.

12. The composition as in one of embodiments 6 to 11, wherein the 1-chloro-3,3,3-trifluoropropene is in trans form in a weight proportion greater than or equal to 90%, preferably greater than or equal to 95%, more particularly preferably greater than or equal to 98%, even more particularly preferably greater than or equal to 99%, and ideally greater than or equal to 99.5%, or even greater than 99.9%.

13. The composition as in one of embodiments 6 to 12, also comprising one or more heat-transfer compounds other than 1-chloro-3,3,3-trifluoropropene and/or one or more additives chosen from stabilizers other than the alkene compound, lubricants, surfactants, tracers, fluorescent agents, odorous agents, solubilizing agents, and mixtures thereof.

14. The use of a composition as in one of embodiments 6 to 13 as a heat-transfer fluid in a vapor compression system.

15. The use as in embodiment 14, wherein the vapor compression system is:

an air-conditioning system; or a refrigeration system; or a freezing system; or a heat pump system.

16. The use of a composition as in one of embodiments 6 to 13 as a heat-transfer fluid in a thermal engine.

17. The use as in one of embodiments 14 to 16, wherein the heat-transfer fluid is at a temperature greater than or equal to 100° C., preferably greater than or equal to 140° C., more particularly preferably greater than or equal to 180° C., for at least one fraction of the duration of its use.

18. The use as in one of embodiments 14 to 17, wherein the heat-transfer fluid is evaporated in a flooded evaporator.

19. A heat transfer facility comprising a circuit containing a composition as in one of embodiments 6 to 13 as a heat-transfer fluid.

20. The facility as in embodiment 19, chosen from mobile or stationary facilities for heating via a heat pump, for air-conditioning, for refrigeration or for freezing and thermal engines.

21. The facility as in embodiment 19 or 20, comprising a flooded evaporator.

22. A process for heating or cooling a fluid or a body by means of a vapor compression system containing a heat-transfer fluid, said process comprising successively the evaporation of the heat-transfer fluid, the compression of the heat-transfer fluid, the condensation of the heat-transfer fluid and the expansion of the heat-transfer fluid, wherein the heat-transfer fluid is a composition as in one of embodiments 6 to 13.

23. A process for producing electricity by means of a thermal engine, said process comprising successively the evaporation of the heat-transfer fluid, the expansion of the heat-transfer fluid in a turbine which makes it possible to generate electricity, the condensation of the heat-transfer fluid and the compression of the heat-transfer fluid, wherein the heat-transfer fluid is a composition as in one of embodiments 6 to 13.

The invention claimed is:

1. A process for heating or cooling a fluid or a body with a vapor compression system containing a heat-transfer fluid, said process comprising, successively:
   evaporating the heat-transfer fluid,
   compressing the heat-transfer fluid,
   condensing the heat-transfer fluid, and
   expanding the heat-transfer fluid,
   wherein the heat-transfer fluid is a composition comprising 1-chloro-3,3,3-trifluoropropene and a mixture comprising 2-methylbut-1-ene and 2-methylbut-2-ene.

2. The process of claim 1, wherein the heat transfer fluid is at a temperature, at at least one point, greater than or equal to 100° C.

3. The process of claim 1, wherein the heat transfer fluid is at a temperature, at at least one point, greater than or equal to 140° C.

4. The process of claim 1, wherein the vapor compression system comprises a heat pump, wherein the heat-transfer fluid is at a temperature of at least 140° C. over at least 50% of its complete circulation time.

5. The process of claim 1, wherein the heat transfer fluid is at a temperature, at at least one point, greater than or equal to 200° C.

6. The process of claim 1, wherein the process is a cooling process.

7. The process of claim 1, wherein the composition comprises from 0.01% to 5% of the mixture comprising 2-methylbut-1-ene and 2-methylbut-2-ene.

8. The process of claim 1, wherein the composition comprises from 0.2% to 1% of the mixture comprising 2-methylbut-1-ene and 2-methylbut-2-ene.

9. The process of claim 1, wherein the 1-chloro-3,3,3-trifluoropropene is in trans form in a weight proportion greater than or equal to 90%.

10. The process of claim 1, wherein the 1-chloro-3,3,3-trifluoropropene is in trans form in a weight proportion greater than or equal to 99%.

11. The process of claim 1, wherein the 1-chloro-3,3,3-trifluoropropene is in trans form in a weight proportion greater than or equal to 99.9%.

12. The process of claim 1, wherein the composition further comprises one or more heat-transfer compounds other than 1-chloro-3,3,3-trifluoropropene and/or one or more additives chosen from stabilizers other than the alkene compound, lubricants, surfactants, tracers, fluorescent agents, odorous agents, solubilizing agents, and mixtures thereof.

13. The process of claim 1, wherein the composition is free of lubricant.

14. A process for producing electricity with a thermal engine, said process comprising, successively:
   evaporating the heat-transfer fluid,
   expanding the heat-transfer fluid in a turbine,
   condensing the heat-transfer fluid, and
   compressing the heat-transfer fluid,
   wherein the heat-transfer fluid is a composition comprising 1-chloro-3,3,3-trifluoropropene and a mixture comprising 2-methylbut-1-ene and 2-methylbut-2-ene.

15. The process of claim 14, wherein the heat transfer fluid is at a temperature, at at least one point, greater than or equal to 100° C.

16. The process of claim 14, wherein the heat transfer fluid is at a temperature, at at least one point, greater than or equal to 140° C.

17. The process of claim 14, wherein the heat transfer fluid is at a temperature, at at least one point, greater than or equal to 200° C.

18. The process of claim 14, wherein the composition comprises from 0.01% to 5% of the mixture comprising 2-methylbut-1-ene and 2-methylbut-2-ene.

19. The process of claim 14, wherein the composition comprises from 0.2% to 1% of the mixture comprising 2-methylbut-1-ene and 2-methylbut-2-ene.

20. The process of claim 14, wherein the 1-chloro-3,3,3-trifluoropropene is in trans form in a weight proportion greater than or equal to 90%.

21. The process of claim 14, wherein the 1-chloro-3,3,3-trifluoropropene is in trans form in a weight proportion greater than or equal to 99%.

22. The process of claim 14, wherein the 1-chloro-3,3,3-trifluoropropene is in trans form in a weight proportion greater than or equal to 99.9%.

23. The process of claim 14, wherein the composition further comprises one or more heat-transfer compounds other than 1-chloro-3,3,3-trifluoropropene and/or one or more additives chosen from stabilizers other than the alkene compound, lubricants, surfactants, tracers, fluorescent agents, odorous agents, solubilizing agents, and mixtures thereof.

24. The process of claim 14, wherein the composition is free of lubricant.

25. A composition comprising 1-chloro-3,3,3-trifluoropropene and a mixture comprising 2-methylbut-1-ene and 2-methylbut-2-ene.

26. The composition of claim 25, comprising from 0.01% to 5% of the mixture comprising 2-methylbut-1-ene and 2-methylbut-2-ene.

* * * * *